United States Patent [19]

Minegishi et al.

[11] 4,102,795

[45] Jul. 25, 1978

[54] SOFTENER COMPOSITION FOR FABRICS OR HAIR

[75] Inventors: Yutaka Minegishi, Miyashiro; Haruhiko Arai, Narashino, both of Japan

[73] Assignee: Kao Soap Co., Ltd., Tokyo, Japan

[21] Appl. No.: 788,408

[22] Filed: Apr. 18, 1977

[30] Foreign Application Priority Data

Apr. 30, 1976 [JP] Japan ................................. 51-50363

[51] Int. Cl.² ........................................... D06M 13/18
[52] U.S. Cl. ........................................ 252/8.9; 252/8.8; 424/62; 424/70
[58] Field of Search ................... 252/8.8; 260/615 B; 424/62, 70

[56] References Cited

U.S. PATENT DOCUMENTS

| | | | |
|---|---|---|---|
| 2,674,619 | 4/1954 | Lundsted | 252/DIG. 1 |
| 2,782,240 | 2/1957 | Hefner et al. | 260/615 B |
| 2,828,345 | 3/1958 | Spriggs | 260/615 B |
| 3,538,033 | 11/1970 | Hayashi et al. | 260/615 B |
| 3,539,519 | 11/1970 | Weimer | 260/615 B |
| 3,936,538 | 2/1976 | Marshall et al. | 252/8.8 |

*Primary Examiner*—William E. Schulz
*Attorney, Agent, or Firm*—Blanchard, Flynn, Thiel, Boutell & Tanis

[57] ABSTRACT

A composition for softening fabrics or hair consisting essentially of an aqueous solution or dispersion containing 3 to 20 weight percent of a cationic amine derivative capable of softening fabrics or hair and 0.005 to 1.0 weight percent of a polyoxyalkylene derivative obtained by reacting an adduct of 20 to 300 moles of ethylene oxide, propylene oxide or mixture thereof to a monohydric alcohol, a monothiolmercaptan or an alkylphenol having from 12 to 26 carbon atoms with from 0.5 to 5 equivalents of a diepoxide, per one equivalent of said adduct.

9 Claims, No Drawings

SOFTENER COMPOSITION FOR FABRICS OR HAIR

BACKGROUND OF THE INVENTION

1. FIELD OF THE INVENTION

The present invention relates to a composition for softening fabrics or hair. More particularly, the present invention relates to a cationic amine derivative composition containing, as a viscosity modifier, a polyoxyalkylene derivative obtained by adding ethylene oxide or a mixture of ethylene oxide and propylene oxide to a monohydric alcohol, a monothiol mercaptan or an alkyl phenol, and reacting the resulting adduct with a diepoxide compound.

2. DESCRIPTION OF THE PRIOR ART

As is well known in the art, cationic amine derivatives having in the molecule at least one alkyl group having 11 to 24 carbon atoms possess excellent properties of softening and rendering anti-electrostatic fabrics, hair and the like, and they are widely used as antistatic softeners for fabrics and as hair rinsing agents.

In general, however, cationic amine derivatives are pasty at high concentrations and their handling is very difficult and troublesome. Accordingly, cationic amine derivatives are ordinarily marketed in the form of aqueous dispersions having a cationic amine derivative concentration of 0.5 to 20% by weight. Although cationic amine derivatives have hydrophilic characteristics, because they have a long-chain alkyl group, the water solubility thereof is low and aqueous solutions of such cationic amine derivatives having relatively high concentrations, such as several percent, are readily gelled. This gelling tendency is promoted when the compositions undergo a temperature change and when the compositions contain a poorly water-soluble component such as a perfume. Further, the presence of even a minute amount of a salt causes a reduction of the viscosity or degrades the dispersed state of the composition. Accordingly, it is required to control very strictly the salt content of cationic amine derivatives and compositions containing same. Even if such strict control is effected, it is very difficult to obtain an aqueous dispersion having a stable selectable viscosity at a selectable concentration of the cationic amine derivative.

In order to solve this problem and to obtain a stable dispersion having a selectable viscosity, it has been attempted to include in the dispersion a non-ionic surface active agent such as a polyoxyethylene alkyl either or an alkyl phenyl ether, a water-soluble macromolecular compound such as hydroxyethyl cellulose or polyethylene glycol or a solvent such as ethylene glycol or ethyl alcohol with a water-soluble salt. However, if the amounts of such additives are small, it is difficult to obtain a stable dispersion of a cationic amine derivative having a certain viscosity. If the additives are incorporated in large amounts, the desired properties of the cationic amine derivatives are degraded. Thus, there has not yet been developed a simple method for dispersing a cationic amine derivative stably at a selectable concentration and a selectable viscosity.

SUMMARY OF THE INVENTION

We have discovered that when an adduct of (i) ethylene oxide or a mixture of ethylene oxide and propylene oxide to (ii) a monohydric alcohol, a monothiol mercaptan or an alkyl phenol is, as disclosed in Japanese Patent Publication No. 32433/70, reacted with a diepoxide compound and the resulting compound is incorporated in an aqueous dispersion or solution of a cationic amine derivative, there is obtained a stable solution or dispersion having a selected viscosity, regardless of the presence of other additives or water-soluble salts, without adversely affecting the softening and antistatic effects and the storage stability of the composition. We have now completed the present invention based on this discovery.

More specifically, in accordance with the present invention, there is provided a composition for softening fabrics or hair which comprises an aqueous solution or dispersion containing (A) 3 to 20% by weight of a cationic amine derivative having in the molecule one or two alkyl groups having from 11 to 24 carbon atoms and (B) 0.005 to 1.0% by weight of a polyoxyalkylene derivative obtained by reacting (1) an adduct of (i) 20 to 300 moles of ethylene oxide, propylene oxide or mixtures thereof to (ii) a compound selected from the group consisting of monohydric alcohols, monothiol mercaptans and alkylphenols having a total carbon atom number of from 12 to 26, with (2) a diepoxide compound in an amount of from 0.5 to 5 equivalents per equivalent of said adduct.

The cationic amine derivative having in the molecule one or two alkyl groups having 11 to 24 carbon atoms is a compound or mixture of compounds selected from the group consisting of quaternary ammonium salts, imidazolinium salts, quaternary amide ammonium salts and cationic polyamides having the following formulae:

I. Quaternary ammonium salts having the formulae:

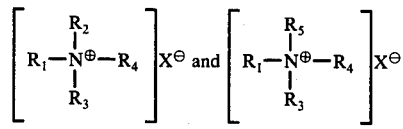

II. Imidazolinium salts having the formula:

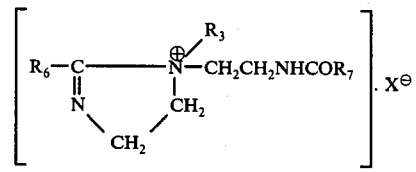

III. Quaternary amide ammonium salts having the formulae:

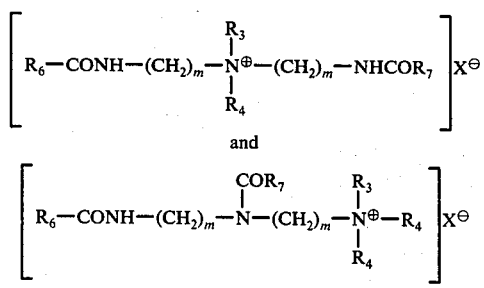

IV. Cationic polyamides obtained by reacting 1 mole of diethylene triamine or dipropylene triamine with about 2 moles of a fatty acid having from 12 to 24 carbon atoms, adding about 1 to about 2 moles of epichlorohydrin to the resulting condensate having an acid value lower than 10, adding an alkaline agent to the adduct to effect ring-opening polymerization and neutralizing the resulting polymer with an acid.

In the foregoing formulae, $R_1$, $R_2$, $R_6$ and $R_7$ each are alkyl having from 11 to 22 carbon atoms or $\beta$-hydroxyalkyl having from 13 to 24 carbon atoms, $R_3$, $R_4$ and $R_5$ each are alkyl having 1 to 3 carbon atoms, benzyl or —$(C_2H_4O)_n$H in which $n$ is a number of from 1 to 3, $m$ is 2 or 3, and X is halogen or monoalkyl sulfate group having 1 to 3 carbon atoms in the alkyl group.

As especially preferred cationic amine derivatives, there can be mentioned (i) di-higher-alkyl dimethyl ammonium chlorides (having 12 to 20 carbon atoms in the higher alkyl group), (ii) 2-higher-alkyl-1-methyl-1-higher-alkanoyl amidoethyl imidazolinium methosulfates (having 12 to 20 carbon atoms in the higher alkyl group and 12 to 20 carbon atoms in the higher alkanoyl group), (iii) di-(higher-alkanoyl-amidoethyl) dimethyl ammonium methosulfates (having 14 to 22 carbon atoms in the higher alkanoyl group), and (iv) compounds obtained by reacting 1 mole of diethylene triamine with 2 moles of a fatty acid having 12 to 20 carbon atoms, adding 1 to 2 moles of epichlorohydrin to the resulting condensate, adding sodium hydroxide to the adduct to effect ring-open polymerization and neutralizing the resulting polymer with glycolic acid.

Quaternary ammonium salts having the formula I can be prepared by a known method, for example, by reacting a trialkyl amine having in the molecule one or two alkyl groups having 11 to 22 carbon atoms or one or two $\beta$-hydroxyalkyl groups having 13 to 24 carbon atoms with an alkyl halide or dialkyl sulfate containing an alkyl group having 1 to 3 carbon atoms.

Imidazolinium salts having the formula II can be prepared, for example, by subjecting 2 moles of a fatty acid having 12 to 24 carbon atoms and 1 mole of diethylene triamine to dehydration condensation at about 200° C and reacting the resulting condensate with 1 mole of an alkyl halide or dialkyl sulfate containing an alkyl group having 1 to 3 carbon atoms.

Quaternary amide ammonium salts having the formula III can be prepared, for example, by subjecting 2 moles of a fatty acid having 12 to 24 carbon atoms and 1 mole of diethylene triamine or dipropylene triamine to dehydration condensation at about 150° C and reacting the resulting condensate with 2 to 3 moles of an alkyl halide or dialkyl sulfate containing an alkyl group having 1 to 3 carbon atoms, in the presence of an alkali catalyst.

As the monohydric alcohol, monothiol mercaptan or alkyl phenol that is used for preparing the polyoxyalkylene derivative (B) in the present invention, the following compounds can be mentioned:

(1) Monohydric alcohols such as dodecyl alcohol, tetradecyl alcohol, hexadecyl alcohol, octadecyl alcohol, arachidic alcohol, docosyl alcohol, octadecenyl alcohol, linoleyl alcohol and abietyl alcohol.

(2) Monothiol mercaptans such as dodecyl mercaptan, tetradecyl mercaptan, hexadecyl mercaptan, octadecyl mercaptan, arachidic mercaptan, docosyl mercaptan and octadecenyl mercaptan.

(3) Alkyl phenols such as octyl phenol, nonyl phenol, decyl phenol, dodecyl phenol, tetradecyl phenol, hexadecyl phenol, octadecyl phenol and arachidic phenol.

The number of moles of ethylene oxide, propylene oxide or mixture thereof to be added is in the range of from 20 to 300. If the amount of propylene oxide added is too high, the resulting polyoxyalkylene derivative is water-insoluble. Accordingly, it is preferred to use ethylene oxide alone or a mixture containing at least 80% by weight of ethylene oxide and up to 20% by weight of propylene oxide. When a mixture of ethylene oxide and propylene oxide is employed, the resulting polyoxyalkylene derivative can be a random or block compound. The preferred number of moles of ethylene oxide and/or propylene oxide to be added is in the range of from 100 to 250.

As the diepoxide compound that is used for the preparation of the polyoxyalkylene derivative, there can be mentioned, for example, vinylcyclohexene diepoxide, limonene diepoxide, 2,2-bis(p-($\beta$,$\gamma$-epoxypropoxy)-phenyl)propane, 1,4-bis($\beta$,$\gamma$-epoxypropoxy)benzene, 1,6-bis(epoxyethyl)hexane, 1,2-bis($\alpha$,$\beta$-epoxypropoxy)butane, 1,3-bis($\beta$,$\gamma$-epoxypropoxy)propane, 1,2-bis($\beta$,$\gamma$-epoxypropoxy)ethane and di-($\alpha$,$\beta$-epoxypropyl)ether. Among these compounds, vinylcyclohexene diepoxide, limonene diepoxide and 2,2-bis(p-($\beta$,$\gamma$-epoxypropoxy)-phenyl)propane are especially preferred.

The polyoxyalkylene derivative can be obtained by reacting, under agitation, one equivalent of an adduct of ethylene oxide and/or propylene oxide to the above-mentioned alcohol, mercaptan or alkyl phenol, with 0.5 to 5 equivalents of a diepoxide compound as mentioned above, at 100° to 150° C, for 30 minutes to 3 hours, in the presence of an alkali catalyst. When the amount used of the diepoxide compound is less than 0.5 equivalents, no viscosity-increasing effect can be obtained, and when the amount of the diepoxide compound is more than 5.0 equivalents, the resulting polyoxyalkylene derivative is water-insoluble.

The amount of the polyoxyalkylene derivative incorporated in the composition is variable depending on the concentration and the specific cationic amine derivative used, the specific other additives used and the concentration and specific type of salt present in the system, but in general, the desired effects can be sufficiently attained when the polyoxyalkylene derivative is incorporated in an amount of 0.005 to 1.0% by weight. Of course, if the amount of the polyoxyalkylene derivative is increased, a composition having a higher viscosity can be obtained. A preferred amount of the polyoxyalkylene derivative is in the range of 0.01 to 0.1% by weight.

Various additives can be incorporated in the composition of the present invention, in accordance with conventional practice. For example, a pigment or dye may be incorporated for improving the appearance of the final product, and a perfume may be incorporated for imparting a good fragrance to the treated fabrics or hair. Moreover, a non-ionic surface active agent may be incorporated for improving the dispersibility of these additives.

The present invention will now be described in greater detail by reference to the following illustrative Examples. The Examples do not limit the scope of the invention.

EXAMPLE 1

In connection with the composition indicated below, the relation between the amount of a polyoxyalkylene derivative incorporated therein and the viscosity of the composition and the storage stability of the composition were examined. The results obtained are set forth in

Table 1.

| Composition: | |
|---|---|
| Distearyl dimethyl ammonium chloride | 6.0% by weight |
| Polyoxyalkylene derivative (A) | 0 to 0.1% by weight |
| Sodium chloride | 0.1% by weight |
| Water | balance |

Note:
The polyoxyalkylene derivative (A) was obtained by reacting alkylene oxide adduct and a diepoxide as set forth in the following Table 2.

Table 1

| Amount (% by weight of Polyoxyalkylene Derivative | Viscosity (cp) (at 25° C) | Storage Stability | |
|---|---|---|---|
| | | 50° C (1 week) | room temp. (4 weeks) |
| 0 | 15 | separation, surface gelation | separation, surface gelation |
| 0.005 | 30 | slight separation | good |
| 0.01 | 50 | good | good |
| 0.03 | 120 | good | good |
| 0.05 | 280 | good | good |
| 0.10 | 740 | good | good |

Comparison 1

The viscosity of an aqueous solution containing 0.1% by weight of the polyoxyalkylene derivative (A) alone was lower than 5 cp.

Comparison 2

The viscosity of a composition formed by incorporating 0.1% by weight of hydroxyethyl cellulose, instead of the polyoxyalkylene derivative (A), in the above composition was 30 cp.

In each run, the viscosity was measured at 25° C by using a BM type viscometer.

As will be apparent from the results shown in Table 1 and the comparisons, a sufficient viscosity-increasing effect cannot be obtained by a conventional viscosity-increasing agent such as hydroxyethyl cellulose, but when a small amount of a polyoxyalkylene derivative is employed in combination with a cationic amine derivative, a synergistic effect is attained whereby the viscosity can be remarkably increased, coupled with good storage stability.

EXAMPLE 2

| Di-hydrogenated-beef-tallow-alkyl dimethyl ammonium chloride | 6.0% by weight |
|---|---|
| Polyoxyalkylene derivative (A) | 0.03% by weight |
| Sodium chloride | 0.1% by weight |
| Water | balance |

EXAMPLE 3

| 2-Heptadecyl-1-methyl-1-(octadecanoylamidoethyl)-imidazolinium methosulfate | 8% by weight |
|---|---|
| Polyoxyalkylene derivative (A) | 0.05% by weight |
| Polyoxyethylene (p=100) lauryl ether | 0.5% by weight |
| Sodium chloride | 1.0% by weight |
| Perfume and pigment | small amounts |
| Water | balance |

EXAMPLE 4

| Di-(octadecanoylamidoethyl) dimethyl ammonium methosulfate | 5% by weight |
|---|---|
| Polyoxyalkylene derivative (A) | 0.1% by weight |
| Sodium chloride | 0.05% by weight |
| Water | balance |

EXAMPLE 5

| Cationic polyamide (K)* | 10% by weight |
|---|---|
| Polyoxyalkylene derivative (A) | 1.0% by weight |
| Polyoxyethylene (p=100) oleyl ether | 0.2% by weight |
| Sodium chloride | 0.1% by weight |
| Pigment | small amount |
| Water | balance |

EXAMPLE 6

| Hydrogenated-rapeseed-oil-alkyltrimethyl ammonium chloride | 6% by weight |
|---|---|
| Polyoxyalkylene derivative (A) | 0.01% by weight |
| Polyoxyethylene (p=100) nonyl-phenyl ether | 1.0% by weight |
| Sodium chloride | 0.05% by weight |
| Perfume and pigment | small amounts |
| Water | balance |

EXAMPLE 7

| Di-hydrogenated-beef-tallow-alkyl dimethyl ammonium chloride | 3% by weight |
|---|---|
| Cationic polyamide (K)* (see Example 5) | 4% by weight |
| Polyoxyalkylene derivative (A) | 0.03% by weight |
| Polyoxyethylene (p=100) lauryl ether | 0.5% by weight |
| Sodium chloride | 0.05% by weight |
| Perfume and pigment | small amounts |
| Water | balance |

EXAMPLE 8

In the composition of Example 2, polyoxyalkylene derivative (B) was used instead of polyoxyalkylene derivative (A).

EXAMPLE 9

In the composition of Example 2, polyoxyalkylene derivative (C) was used instead of polyoxyalkylene derivative (A).

EXAMPLE 10

In the composition of Example 2, polyoxyalkylene derivative (D) was used instead of polyoxyalkylene derivative (A).

EXAMPLE 11

In the composition of Example 2, polyoxyalkylene derivative (E) was used instead of polyoxyalkylene derivative (A).

The alkylene oxides and diepoxides used for the synthesis of polyoxyalkylene derivatives (A) to (E) employed in Examples 1 to 11 are shown in Table 2.

The viscosity and stability of each composition of Examples 2 to 11 are shown in Table 3.

Table 2

| Polyoxyalkylene Derivative | Alkylene Oxide Adduct (a) | Diepoxide (b) | (a)/(b) equivalent Ratio |
|---|---|---|---|
| (A) | polyoxyethylene ($\bar{p}$=200) cetyl ether | vinylcyclohexene diepoxide | 1/0.7 |
| (B) | polyoxyethylene ($\bar{p}$=230) nonylphenyl ether | " | 1/0.5 |
| (C) | dodecyl mercaptan-ethylene oxide adduct ($\bar{p}$=100) | " | 1/2.2 |
| (D) | polyoxyethylene ($\bar{p}$=200) stearyl ether | 2,2-bis(p-($\beta,\gamma$-epoxypropoxy)-phenyl) propane | 1/1 |
| (E) | stearyl alcohol-ethylene oxide ($\bar{p}$=50)-propylene oxide ($\bar{p}$=5) adduct | limonene diepoxide | 1/4 |

Table 3

| | Viscosity (cp) (25° C) | Storage Stability at 50° C (1 week) | at room temp. (4 weeks) |
|---|---|---|---|
| Example 2 | 100 | good | good |
| Example 3 | 85 | good | good |
| Example 4 | 350 | good | good |
| Example 5 | 650 | good | good |
| Example 6 | 60 | almost good | good |
| Example 7 | 170 | good | good |
| Example 8 | 90 | good | good |
| Example 9 | 70 | almost good | good |
| Example 10 | 300 | good | good |
| Example 11 | 800 | good | good |
| Comparison 3 | 12 | separation, surface gelation | separation, surface gelation |
| Comparison 4 | 8 | separation | separaton |
| Comparison 5 | 10 | separation | separation |
| Comparison 6 | 18 | separation | slight separation |
| Comparison 7 | 15 | separation, surface gelation | separation |
| Comparison 8 | 20 | separation | slight separation |

Note:
Comparisons 3 to 8 correspond to the compositions of Examples 2 to 7, except that the polyoxyalkylene derivative was omitted, respectively.
As will be apparent from the results shown in Table 3, in each of comparative compositions 3 to 8, free of the polyoxyalkylene derivative, the viscosity is very low and the storage stability is poor, whereas when a small amount of the polyoxyalkylene derivative is incorporated, a conspicuous viscosity-increasing effect is attained and a good storage stability is manifested.

The embodiments of the invention in which an exclusive property or privilege is claimed are defined as follows:

1. A composition for softening fabrics or hair, said composition being an aqueous solution or dispersion consisting essentially of (A) from 3 to 20 percent by weight of a cationic amine derivative or mixture of said derivatives, said derivatives having in the molecule one or two alkyl groups having 11 to 22 carbon atoms, or one or two $\beta$-hydroxyalkyl groups having 13 to 24 carbon atoms, said derivatives being capable of softening fabric or hair, (B) 0.005 to 1.0% by weight of a water-soluble polyoxyalkylene derivative obtained by reacting an adduct of 20 to 300 moles of ethylene oxide, propylene oxide or mixture thereof to a compound selected from the group consisting of monohydric alcohols, monothiol mercaptans and alkylphenols each having a total carbon atom number of from 12 to 26, with a diepoxide compound in an amount of 0.5 to 5 equivalents of said diepoxide compound per one equivalent of said adduct and (C) the balance of the composition is essentially water.

2. A composition according to claim 1 wherein the cationic amine derivative (A) is a member or a mixture of members selected from the group consisting of (i) di-higher-alkyl dimethyl ammonium chlorides having 12 to 20 carbon atoms in the higher alkyl group, (ii) 2-higher-alkyl-1-methyl-1-higher-alkanoyl amidoethyl imidazolinium methosulfates having 12 to 20 carbon atoms in the higher alkyl group and 12 to 20 carbon atoms in the higher alkanoyl group, (iii) di(higher-alkanoyl-amidoethyl) dimethyl ammonium methosulfates having 14 to 22 carbon atoms in the higher alkanoyl group, and (iv) compounds obtained by reacting 1 mole of diethylene triamine with 2 moles of a fatty acid having 12 to 20 carbon atoms, adding 1 to 2 moles of epichlorohydrin to the resulting condensate, adding sodium hydroxide to the adduct to effect ring-opening polymerization and neutralizing the resulting polymer with glycolic acid.

3. A composition according to claim 1 wherein the amount of the polyoxyalkylene derivative (B) is from 0.01 to 0.1 percent by weight.

4. A composition according to claim 1 wherein the polyoxyalkylene derivative (B) is a compound obtained by reacting an adduct of 20 to 300 moles of ethylene oxide or a mixture comprising at least 80% by weight of ethylene oxide and up to 20% by weight of propylene oxide to a monohydric alcohol having 12 to 20 carbon atoms or an alkyl phenol having 8 to 16 carbon atoms in the alkyl group, with a diepoxide compound in an amount of 0.5 to 5 equivalents of said diepoxide compound per one equivalent of the adduct.

5. A composition according to claim 2 wherein the polyoxyalkylene derivative (B) is a compound obtained by reacting an adduct of 20 to 300 moles of ethylene oxide or a mixture comprising at least 80% by weight of ethylene oxide and up to 20% by weight of propylene oxide to a monohydric alcohol having 12 to 20 carbon atoms or an alkyl phenol having 8 to 16 carbon atoms in the alkyl group, with a diepoxide compound in an amount of 0.5 to 5 equivalents of said diepoxide compound per one equivalent of the adduct.

6. A composition according to claim 1 wherein the diepoxide compound is one member or a mixture of members selected from the group consisting of vinylcyclohexene diepoxide, limonene diepoxide and 2,2-bis(p-($\beta,\gamma$-epoxypropoxy)phenyl)propane.

7. A composition according to claim 1 wherein the cationic amine derivative is a compound having the formula:

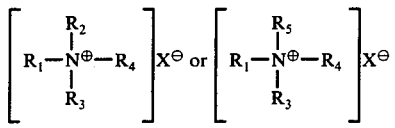

wherein $R_1$ and $R_2$ is alkyl having 11 to 22 carbon atoms or $\beta$-hydroxyalkyl having 13 to 24 carbon atoms, $R_3$, $R_4$ and $R_5$ each are alkyl having 1 to 3 carbon atoms, benzyl or $-(C_2H_4O)_nH$ in which $n$ is a number of from 1 to 3, and X is halogen or monoalkyl sulfate group having 1 to 3 carbon atoms in the alkyl group.

8. A composition according to claim 5 wherein the cationic amine derivative is a compound having the formula:

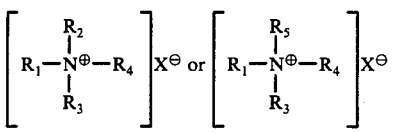

wherein $R_1$ and $R_2$ is alkyl having 11 to 22 carbon atoms or β-hydroxyalkyl having 13 to 24 carbon atoms, $R_3$, $R_4$ and $R_5$ each are alkyl having 1 to 3 carbon atoms, benzyl or —$(C_2H_4O)_nH$ in which $n$ is a number of from 1 to 3, and X is halogen or monoalkyl sulfate group having 1 to 3 carbon atoms in the alkyl group.

9. A composition according to claim 1 in which said cationic amine derivative (A) is selected from the group consisting of quaternary ammonium salts having the formulae

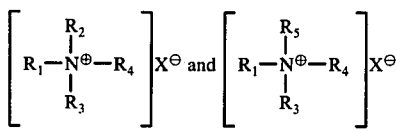

imidazolinium salts having the formula

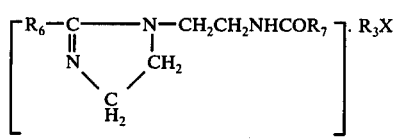

quaternary amide ammonium salts having the formulae

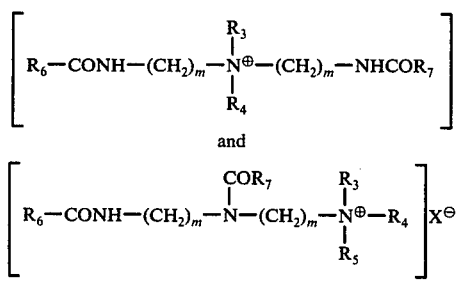

wherein $R_1$, $R_2$, $R_6$ $R_7$, which can be the same or different, each are alkyl having 11 to 22 carbon atoms or β-hydroxyalkyl having 13 to 24 carbon atoms; $R_3$, $R_4$ and $R_5$ are alkyl having one to 3 carbon atoms, benzyl or —$(C_2H_4O)_mH$ in which $n$ is a number from one to 3, $m$ is 2 or 3, $n$ and X is halogen or monoalkyl sulfate having one to 3 carbons in the alkyl group, and cationic polyamides obtained by reacting one mole of diethylene triamine or dipropylene triamine with about 2 moles of a fatty acid having 12 to 24 carbon atoms, adding about one to about 2 moles of epichlorohydrin to the resulting condensate having an acid value lower than 10, adding an alkaline agent to the adduct to effect ring-opening polymerization and neutralizing the polymer with an acid, said monohydric alcohol is selected from the group consisting of dodecyl alcohol, tetradecyl alcohol, hexadecyl alcohol, octadecyl alcohol, arachidic alcohol, docosyl alcohol, octadecenyl alcohol, linoleyl alcohol and abietyl alcohol, said monothiol mercaptan is selected from the group consisting of dodecyl mercaptan, tetradecyl mercaptan, hexadecyl mercaptan, octadecyl mercaptan, arachidic mercaptan, docosyl mercaptan and octadecenyl mercaptan, said alkyl phenol is selected from the group consisting of octyl phenol, nonyl phenol, decyl phenol, dodecyl phenol, tetradecyl phenol, hexadecyl phenol, octadecyl phenol and arachidic phenol, said adduct containing from 100 to 250 moles of ethylene oxide or a mixture containing up to 20 weight percent of propylene oxide and the balance is ethylene oxide, said diepoxide compound is selected from the group consisting of vinylcyclohexene diepoxide, limonene diepoxide, 2,2-bis(p-(β,γ-epoxypropoxy)-phenyl)propane, 1,4-bis(β,γ-epoxypropoxy)benzene, 1,6-bis(epoxyethyl)hexane, 1,2-bis(α,β-epoxypropoxy)butane, 1,3-bis(β,γ-epoxypropoxy)ethane and α,β-epoxypropyl ether, and the reaction of said adduct with said diepoxide is performed at 100° to 150° C, for from 30 minutes to 3 hours, in the presence of an alkali catalyst.

* * * * *